United States Patent [19]
Saripalli et al.

[11] Patent Number: 5,744,709
[45] Date of Patent: Apr. 28, 1998

[54] MEASUREMENT OF SPECIFIC INTERFACIAL AREAS OF IMMISCIBLE FLUID INTERFACES IN FLOW SYSTEMS

[75] Inventors: Kanaka Prasad Saripalli; P. S. C. Rao; Michael D. Annable; Kirk Hatfield, all of Gainesville, Fla.

[73] Assignee: University of Florida, Gainesville, Fla.

[21] Appl. No.: 641,141

[22] Filed: Apr. 25, 1996

[51] Int. Cl.⁶ .......................... B01D 15/04; G01N 15/08; C12Q 01/02
[52] U.S. Cl. ........................... 73/152.18; 73/152.31; 73/152.55; 73/152.42; 73/53.06; 166/270; 166/310
[58] Field of Search .................... 73/152.18, 152.29, 73/152.31, 152.42, 152.55, 61.62, 40.7, 53.06, 155.55; 166/270, 300, 310

[56] References Cited

U.S. PATENT DOCUMENTS

| | | | |
|---|---|---|---|
| 2,909,923 | 10/1959 | Miller | 73/155 |
| 3,187,567 | 6/1965 | O'Brien et al. | 73/155 |
| 4,232,738 | 11/1980 | Yen et al. | 166/274 |
| 4,596,283 | 6/1986 | Ciprios et al. | 165/1 |
| 4,672,840 | 6/1987 | Cullick | 73/38 |
| 4,832,850 | 5/1989 | Cais et al. | 210/638 |
| 4,941,533 | 7/1990 | Buller et al. | 166/252 |
| 5,030,453 | 7/1991 | Lenk et al. | 424/450 |
| 5,225,332 | 7/1993 | Weaver et al. | 435/29 |
| 5,542,935 | 8/1996 | Unger et al. | 604/190 |
| 5,550,761 | 8/1996 | Pauchon et al. | 364/578 |

*Primary Examiner*—Richard Chilcot
*Assistant Examiner*—J. David Wiggins
*Attorney, Agent, or Firm*—Quarles & Brady

[57] ABSTRACT

This invention relates generally to methods of measuring interfacial areas, and more specifically to flow-based methods for measuring the area of the interfaces between two immiscible fluids. The immiscible fluids of interest are various oils and gases that do not have significant solubility, and thus form a distinct fluid phase and exist as agglomerations of varying sizes of blobs or ganglia when added to aqueous solutions. Our invention permits the measurement of such fluid-fluid interface areas for two immiscible fluids present in flow systems. The flow-based method involves the introduction of an interfacial tracer chemical into the flow system in one of two modes: (1) step input, and (2) pulse input. The tracer is soluble to appreciable extent in only one of the two fluids, designated as the carrier fluid phase. The average rate of the tracer migration through the flow system is measured and compared with the rate of migration of a non-adsorbing reference tracer which is added along with the interfacial tracer. The amount of the tracer adsorbed is calculated from the amount of the interfacial tracer adsorbed and from the relative migration rates of the interfacial and reference tracers through the flow system. The total fluid-fluid interfacial area present in the flow system is then calculated based on the amount of the interfacial tracer adsorbed and the interfacial area occupied by each of the interfacial tracer molecules.

15 Claims, 9 Drawing Sheets

5,744,709

MEASUREMENT OF SPECIFIC INTERFACIAL AREAS OF IMMISCIBLE FLUID INTERFACES IN FLOW SYSTEMS

BACKGROUND OF THE INVENTION

1. Field of the Invention

This invention relates generally to methods of measuring interfacial areas, and more specifically to methods for measuring the area of fluid-fluid interfaces between two immiscible fluids in flow systems.

2. Description of the Relevant Art

Solid-liquid and liquid-liquid interfaces play a very important role in a variety of physical-chemical-biological processes relevant in environmental and chemical engineering application. See A. W. Adamson, *Physical Chemistry of Surfaces*, John Wiley & Sons, New York, N.Y., 1982. Behavior of immiscible fluids co-existing in flow systems is of fundamental interest in several sciences, including environmental science, surface science and engineering, hydrogeology, soil science, food technology, petroleum engineering and chemical engineering. See A. T. Corey, *Mechanics of Immiscible Fluids in Porous Media*, Water Resources Publications, Littleton, Colo., 1985. As used in the specifications and claims, we use the term flow system to represent a test volume element containing two immiscible fluids either in the presence or absence of solid phase, and through which flow of at least one fluid at some constant or variable rate is established. Two specific examples of the flow system schematics are illustrated in FIG. 1. We also use the term immiscible fluids to represent two fluids that do not dissolve in each other to an appreciable extent, and therefore form distinct fluid-fluid interfaces. Our present invention permits the measurement of the areas of such fluid-fluid interfaces in flow systems.

Immiscible fluids such as air, water and oil, co-exist in many natural and synthetic flow systems, including soils, aquifers, petroleum reservoirs and packed beds. Similarly, emulsions or dispersions of oil-water or gas-water without the presence of a solid phase (either as a packing or as a fluidized bed) are encountered in various chemical processing units, for example in food and cosmetic manufacturing industries. Organic liquids (such as coal tar, gasoline, and industrial solvents) found at the hazardous waste sites, are another important example of oils as immiscible fluids co-existing in a flow system. Petroleum engineers are interested in recovering immiscible fluids such as crude oil for use as fuels, while environmental scientists and engineers are faced with the challenge of characterizing and remediating the immiscible organic liquid wastes distributed in subsurface flow systems, which is in the soil material under earth's surface extending into the aquifiers, in order to prevent soil and groundwater contamination. In water-unsaturated subsurface flow systems, it is of interest to characterize the amount and distribution of gases and water. Scientists and engineers performing these operations need to know how much immiscible fluid (e.g., oil or gas phase) there is in the flow system, and how it is spatially distributed. For these reasons, determining the total amount of spatial distribution of the immiscible fluid phases, and the fluid-fluid interfacial areas, is important.

The volume of an immiscible fluid i per unit fluid volume of the flow system is known as the fluid saturation $S_i$. The area of interface between two immiscible fluids i and j per unit volume of flow system is known as the specific fluid-fluid interfacial area $\alpha_{ij}$. Fluid saturations and specific fluid-fluid interfacial areas are two important characteristics necessary to understand the fate, distribution, transport and morphology of immiscible fluids in flow systems, as well as the heat, mass and momentum transfer processes at the fluid-fluid interfaces.

Tracer methods and liquid extraction techniques are available to measure $S_i$ (For a tracer technique to measure $S_i$ see Jin et al. 1955). However, no methods are currently available to measure $\alpha_{ij}$ in flow systems. The measurement of the interfacial area of immiscible fluids can present a significant challenge. In many flow systems, one fluid phase is dispersed as an immiscible phase in the other fluid as agglomerations of varying sizes. This precludes the possibility of calculating the interfacial area from parameters that are readily observed. The present invention offers a tracer method to measure $\alpha_{ij}$ in flow systems containing two immiscible fluids.

In many engineering applications, laboratory and field tracer experiments are routinely conducted and the data are analyzed using theory and computer models. A tracer is a chemical compound which, when introduced into the flow system, chemically interacts with the system in a specific way. Observations of the manner in which an injected pulse of tracer solution is displaced through the flow system enables the characterization of the hydrodynamics of the flow system as well the quantity, distribution, and transport of immiscible fluids in the flow system. For example, non-reactive tracers (i.e., those chemical species that do not in any adsorb to any solid or fluid component of the flow system) have been used to characterize the hydrodynamics of fluid flow in flow systems. See Hutchins et al, 1993, U.S. Pat. No. 5,246,860; Satter et al., 1981, U.S. Pat. No. 4,278, 128. Chemical tracers that dissolve and partition into the immiscible fluid phases present in flow systems have also been used to characterize the flow dynamics and the amount of immiscible fluids in flow systems. See Simmons et al., 1985, U.S. Pat. No. 4,520,109; Carter et al., 1980, U.S. Pat. No. 2,231,426; Jin et al., Water Resour. Res. 31, 1201 1995). The disclosures of these references are fully incorporated by references.

Use of adsorbing gaseous tracer molecules, such as nitrogen, to measure the specific solid-fluid surface areas of porous solids is a well established technique. In this technique, the solid-fluid specific surface area is measured as the product of the average area occupied by a single tracer molecule adsorbed at the solid surface, and the number of tracer molecules covering the solid surface as a monolayer at saturation adsorption. See M. J. Rosen, *Surfactants and Interfacial Phenomena*, John Wiley & Sons, New York, N.Y., 1978; A. W. Adamson, *Physical Chemistry of Surfaces*, John Wiley & Sons, New York, N.Y., 1982; S. G. Gregg and K. S. W. Sing, *Adsorption, Surface Area and Porosity*, Academic Press, London, 1982; D. L. Carter, M. M. Mortland, and W. D. Kemper, in *Methods of Soil Analysis*, American Society of Agronomy, Inc. and Soil Science Society of America, Inc., Madison, Wis. 1986 (Chapter 16). While adsorbing tracers have been used to measure solid-fluid interfacial areas, no technique has heretofore been developed to utilize adsorbing tracer molecules to measure the fluid-fluid interfacial area of substantially immiscible fluids in flow systems.

SUMMARY OF THE INVENTION

It is an object of the invention to provide a method to measure the fluid-fluid interfacial area between two immiscible fluids in flow systems.

It is another object of the invention to provide flow-based methods to measure the area of immiscible fluid-fluid interfaces in subsurface flow systems.

These and other objects are provided by a method for measuring the fluid-fluid interfacial area of between two substantially immiscible fluids. The method involves "step input" or a "pulse input" addition of an interfacial tracer compound soluble in one of the two immiscible fluids is added to a first of said fluids, which is designated as the "carrier" fluid phase. Thus, one of the said fluids is the mobile phase that carries the tracers, while the other can be either at rest or in a state of motion within the flow system. An interfacial tracer is a chemical species that is soluble in first of said fluids, adsorbs as a monolayer at the immiscible fluid-fluid interface of interest, but does not partition into the second of said immiscible fluids. A pulse input is a relatively small volume of tracer solution added to the flow system influent, whereas a step input is a larger volume of tracer solution added in the influent until the influent and effluent tracer concentration response becomes equal. For further detail see O. Livenspiel, 1972, *Chemical Reaction Engineering*, John Wiley & Sons, NY. In both cases, the interfacial tracer will accumulate as a monolayer at the fluid-fluid interface, but will not partition into the second of the said fluids. The response of interfacial tracer, usually mass concentration (mg/L), in the first of the said fluids exiting the flow system is measured as a function of time.

In the case of step input, the amount of interfacial tracer that has adsorbed at the interface as a monolayer is calculated. The interfacial area, $\alpha_{ij}$, is then calculated from the amount of tracer compound that has adsorbed at the interface as a monolayer. The fluid-fluid interfacial area is calculated according to the formula $\alpha_{ij}=\alpha N$, where $\alpha$ is the area occupied by a single tracer molecule and N is the amount of interfacial tracer in terms of total tracer molecules that has formed the monolayer. This method assumes complete coverage of the fluid-fluid interfacial area by the interfacial tracer.

In most instances, however, it will not be practical to use the step-input method described above. In the second method, designated the pulse-input method, a non-reactive tracer that does not adsorb at the fluid-fluid interface or partitions into the second of said fluids must be used along with the interfacial tracer to determine the relative rates of migration of the two tracers through the flow system. Interfacial tracer accumulates at the fluid-fluid interface of interest from the first of the said fluids such that the proportion of interfacial tracer mass concentration on the interface to that in the first of the said fluids remains essentially constant, the constant of proportionality being referred to as an "adsorption coefficient", $K_{ij}$. The adsorption coefficient is a constant, specific to a given tracer, a given immiscible fluid interface, and the composition of the two fluid phases. Because the interfacial tracer accumulates at the immiscible fluid-fluid interface where as the non-reactive tracer does not, and the rate of migration of the interfacial tracer is slower than that of the non-reactive tracer. Retardation Factor, $R_i$, which is a relative measure of the velocity at which the non-reactive tracer and the interfacial tracer move through the flow system, together with the adsorption coefficient, $K_{ij}$, is used to determine the interfacial area that is adsorbing the interfacial tracer.

The selection of the interfacial tracer will depend on the particular fluid-fluid system that is of interest. In the case of oil-water or air-water systems, such as are frequently encountered in the subsurface flow systems, surfactants are useful as interfacial tracers. In particular, various anionic surfactants are especially suitable, since they have insignificant solubility in the oil or air phase, high solubility in aqueous solutions, and do not sorb to the solid matrix (when present) in significant amounts.

In summary, the method of the invention can be used to measure the area of interfaces formed by two immiscible fluid interfaces present in flow systems, using surfactants as interfacial tracers and non-reactive tracers in tandem.

BRIEF DESCRIPTION OF THE DRAWINGS

There are shown in the drawings embodiments that are presently preferred, it being understood, however, that the invention is not limited to the precise arrangements and instrumentalities that are shown, wherein.

DETAILED DESCRIPTION OF THE PREFERRED EMBODIMENTS

The invention permits the measurement of the interfacial area between two immiscible fluids present in a flow system by the utilization of interfacial tracers. Interfacial tracers are defined as chemical species that accumulate at the fluid-fluid interface by adsorption, but dissolve into only one of the two fluids, which is defined here as the carrier fluid. The four assumptions that are made in using interfacial tracers for measuring interfacial area are that:

(1) the interfacial tracer adsorbs at the said fluid-fluid interface of interest, but does not dissolve in measurable quantities into the second fluid phase;

(2) the interfacial tracer does not adsorb to a measurable extent at any interfaces other than the said fluid-fluid interface of interest;

(3) the adsorption of the interfacial at the said fluid-fluid interface occurs as a monolayer coverage; and (4) each adsorbed tracer molecule occupies a constant, known molecular area at the fluid-fluid interface.

These assumptions are reasonable in a number of fluid-fluid systems, permitting use of the invention to measure the fluid-fluid interfacial area in flow systems.

Two specific methods are described here for measuring the fluid-fluid interfacial area, aij, in flow systems using the interfacial tracers adsorption; the step-input method, and the pulse-input method. In both of these methods, a known volume of solution of interfacial tracer of known and fixed concentration, Co, is introduced into the flow system by addition with the carrier fluid, and the tracer concentration in the carrier fluid exiting the flow system is monitored. In both methods, the total volume of the carrier fluid in the flow system, designated as the pore volume (P), is measured by conducting a similar experiment using nonreactive tracer which does not adsorb or dissolve into the immiscible fluid which is not the carrier fluid.

Figure 1A:
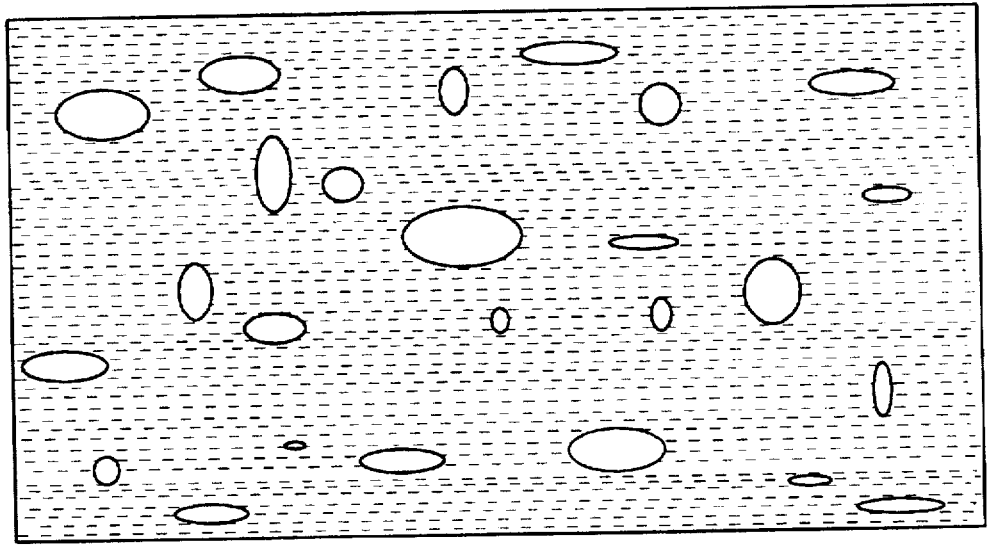
FIG. 1 is a schematic representation of two types of flow systems in which the immiscible fluids are distributed.
Figure 1B:
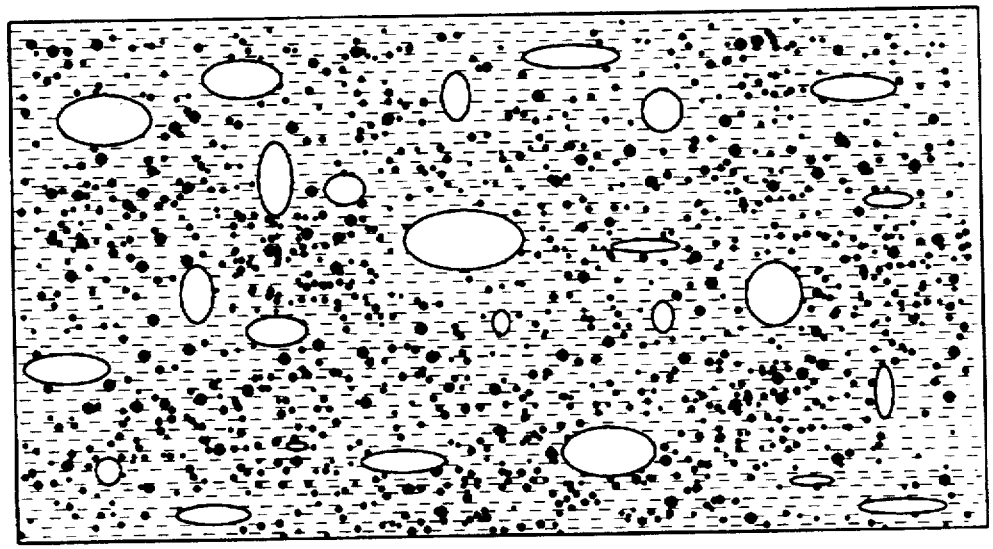

In the step-input method, the interfacial and nonreactive tracer solutions are introduced until the measured exit concentrations of both interfacial and nonreactive tracer solutions are equal to that in the injected carrier fluid. A description of this approach is contained Nkdi-kisa, P. et al., "Influence of Organic Cosolvents on Leaching of Hydrophobic Organic Chemicals Through Soils, Envir. Science & Tech. Vol. 21, 1107, the disclosure of which is fully incorporated by reference. A typical tracer response curve, designated as the breakthrough curve (BTC), monitored in the exiting carrier fluid, is illustrated in FIG. 1. The area, $A_{NR}$, above the BTCs for the nonreactive tracer is used to calculate P, the pore volume as defined earlier. The area, $A_{IT}$, above the BTC for the interfacial tracer, is used to calculate the total mass, M, of the interfacial tracer adsorbed within the flow system. Note that, $$\text{area above } BTC = \int_0^{p_f} (1 - C/C_o) dp \quad (1)$$

where p represents number of pore volumes of carrier fluid flown through the flow system at any stage of the input experiment and $p_f$ is the total number of pore volumes of carrier fluid flown through the flow system to complete the step-input experiment. Then, the total mass of interfacial tracer adsorbed, M, is given as:

$$M = (A_{IT} - A_{NR}) C_o P \quad (2)$$

Using interfacial tracer adsorption method, the $\alpha_{ij}$(cm$^2$/cm$^3$) of an immiscible fluid interface in a flow system of total volume V (cm$^3$) can be obtained by the following equation:

$$a_{ij} = MN \frac{a}{Vm10^{19}} \quad (4)$$

where M (mg) is the mass of an interfacial tracer adsorbed at equilibrium from carrier fluid, $\alpha$(Å$^2$) is the area per molecule of interfacial tracer adsorbed at the fluid-fluid interface as a monolayer, N is Avogadro's number and m (gm/mole) is the interfacial tracer molecule weight.

The fluid-fluid interfacial area can be calculated directly from the amount of interfacial tracer that has formed the monolayer. The fluid-fluid interfacial area can be determined according to the formula $\alpha_{ij} = \alpha T$, where $\alpha$ is the area of a single tracer molecule and T is the number of molecules of interfacial tracer that have formed the monolayer. The area occupied by each interfacial tracer molecule, $\alpha$, can be determined by any appropriate method; the method that is presently preferred utilizes an analysis of tracer adsorption isotherm data using the Gibbs' model. The theory of the Gibbs' model is described in M. J. Rosen, *Surfactants and Interfacial Phenomena*, John Wiley & Sons, NY, N.Y. (1978) pgs 55–60, and S. G. Oh and D. O. Shah, "Effect of Counterions on the Interfacial Tension and Emulsion Droplet Size in the Oil/Water/Dodecyl Sulfate System", *The Journal of Physical Chemistry*, 1993, 97. The disclosures of these documents are incorporated by reference. The interfacial tension $\gamma$ is measured as a function of the tracer concentration.

In the pulse-input method, a non-reactive tracer is used in tandem with an interfacial tracer to determine a Retardation Factor, $R_f$, which is a relative measure of the rate at which the centers-of-mass of the pulses of the non-reactive and the interfacial tracers move through the test volume in a flow system. The center-of-mass of the tracer pulse is calculated as the centroid of the injected pulse as it travels through the test volume. The retardation factor is used to determine the fluid-fluid interfacial area that is adsorbing the interfacial tracer. The non-reactive tracer provides a comparative measure of the rate at which a similar molecule moves through the flow system, except for the adsorption effects of the fluid-fluid interface. A comparison of the two rates will isolate the effects on the rate of travel of the interfacial tracer that are due to adsorption at the interface.

To illustrate the measurement of $\alpha_{ij}$ using pulse-input method, a flow system can be considered which contains an immiscible fluid-fluid interface through which the carrier fluid is flowing at a constant rate. At time zero, a pulse of a nonreactive tracer and an interfacial tracer, of known concentration $C_o$, is introduced in the carrier fluid at the inlet for a duration of $t_s$. The rate of travel of the interfacial tracer through the flow system is retarded relative to the non-reactive tracer, due to adsorption at the immiscible fluid-fluid interface, which is measured by a 'Retardation Factor', $R_f$, defined from advection-dispersion theory of reactive solute transport through porous media (See R. A. Freeze and J. A. Cherry, 1979, *Ground Water*, Prentice Hall, Inc., Englewood Cliffs, N.J.), as:

$$R_f = \frac{\mu_{IT}}{\mu_{NR}} = 1 + \frac{a_{ij} K_{ij}}{\theta_i} \quad (4)$$

where $\mu$, is the centroid of a tracer pulse, with the subscripts IT and NR referring respectively to the interfacial and non-reactive tracers. The centroid of each tracer pulse is calculated as:

$$\mu = \frac{\int_0^\infty C(t) t \, dt}{\int_0^\infty C(t) \, dt} - \frac{t_s}{2} \quad (5)$$

Here, C(t) is the eluent tracer concentration monitored at the flow system outlet, $\theta_i$ is the carrier fluid content expressed as a volume fraction and $K_{ij}$ is a linear adsorption coefficient, obtained as the slope of the Gibbs' adsorption isotherm, and $t_s$ is the duration (hours) during which the tracer pulse is introduced.

Equation 2 is based on the assumption of reversible, equilibrium adsorption and a linear isotherm, implying a constant $K_{ij}$ for a surfactant at a given immiscible fluid-fluid interface, and also assumes that no other sinks and sources for the interfacial tracer are present in the flow system.

Adsorption of interfacial tracers from dilute aqueous solutions at an oil-water interface or air-water interface can be described using Gibbs' adsorption isotherm (3) as below:

$$\Gamma = -\frac{1}{RT} C(\partial \gamma / \partial C) \quad (6)$$

where $\Gamma$ (mole/m$^2$) is the Gibbs' surface excess of surfactant, $\gamma$ (Joules/m$^2$) is the interfacial tension at the fluid-fluid interface. C is the aqueous phase molar concentration of surfactant, R is universal gas constant and T (°K.) is temperature. Activity of surfactant monomers remains constant in the supra-CMC concentration range as micelles begin to form at the CMC (5), leading to adsorption saturation near and above the CMC. If the slope of $\gamma$ versus C plot, ($\delta\gamma/\delta C$), is a constant over a limited range of surfactant concentration, then the interfacial tracer adsorption isotherm becomes linear in that concentration range, and can be represented by the equation $\Gamma=K_{ij}C$, where $K_{ij}$ is equal to $-(1/RT)(\delta\gamma/\delta C)$.

Anionic surfactants are excellent candidates for use as interfacial tracers, in both air-water and oil-water systems, with their insignificant solubility in the oil or air phases and high water solubility values (3). It is reasonable to assume that anionic surfactants adsorbing at a hydrophobic oil-water interface or air-water interface attain monolayer, saturation adsorption coverage at the critical micellar concentration or CMC of the surfactant. CMC is the concentration at which surfactant monomers self-aggregate and form clusters called miscelles (2). Anionic surfactant monomers at the carbon/aqueous interface, a model hydrophobic surface, were found to exhibit a saturation monolayer coverage of the interface at the CMC (3,6). Anionic surfactants adsorb at the hydrophobic oil-water interface or air-water interface with the hydrophilic head groups oriented towards the aqueous phase. A bilayer formation on the resulting negatively charged interface is not likely.

Described in the following sections are experiments conducted using sodium dodecyl benzenesulfonate (SDBS) as an interfacial tracer to measure $\alpha_{ij}$ in porous media containing decane or air, with aqueous solutions being the carrier fluid. Batch experiments verified that the anionic surfactant SDBS does not partition into the bulk oil phases, such as tetrachloroethane and decane, its oil-solubility being extremely low. Being non-volatile, SDBS does not partition into the air phase either.

Experimental Demonstration

To demonstrate the method and application of interfacial tracers, we conducted two sets of experiments in porous media (i.e., packings of glass beads and clean sand), using decane-water and air-water pairs as the immiscible fluids. These experimental examples represent two diverse fields of application of the interfacial tracer technology. Decane-water experiments represent porous media containing oil and water, such as petroleum fields and hazardous waste oil contaminated aquifiers. The air-water experiments represent the unsaturated zone of the sub-surface, where air and water co-exist. Accordingly, the experimental results and interpretation are presented in separate sections below:

EXAMPLE 1

Decane-Water Experiments

Figure 2:
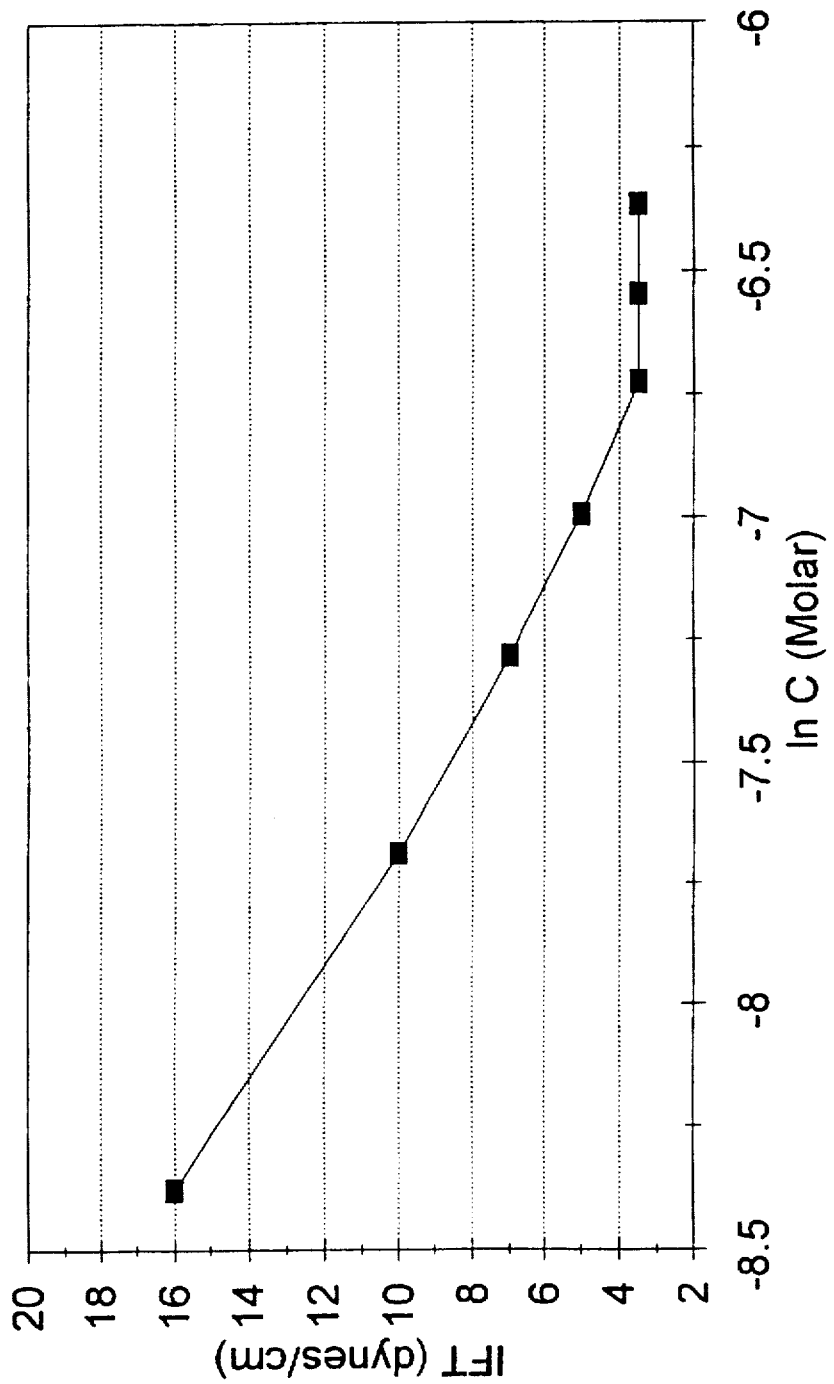
FIG. 2 is a graph of the change in Gibb's surface excess and interfacial tension due to adsorption of the interfacial tracer (SDBS) at decane-water interface.
Figure 3:
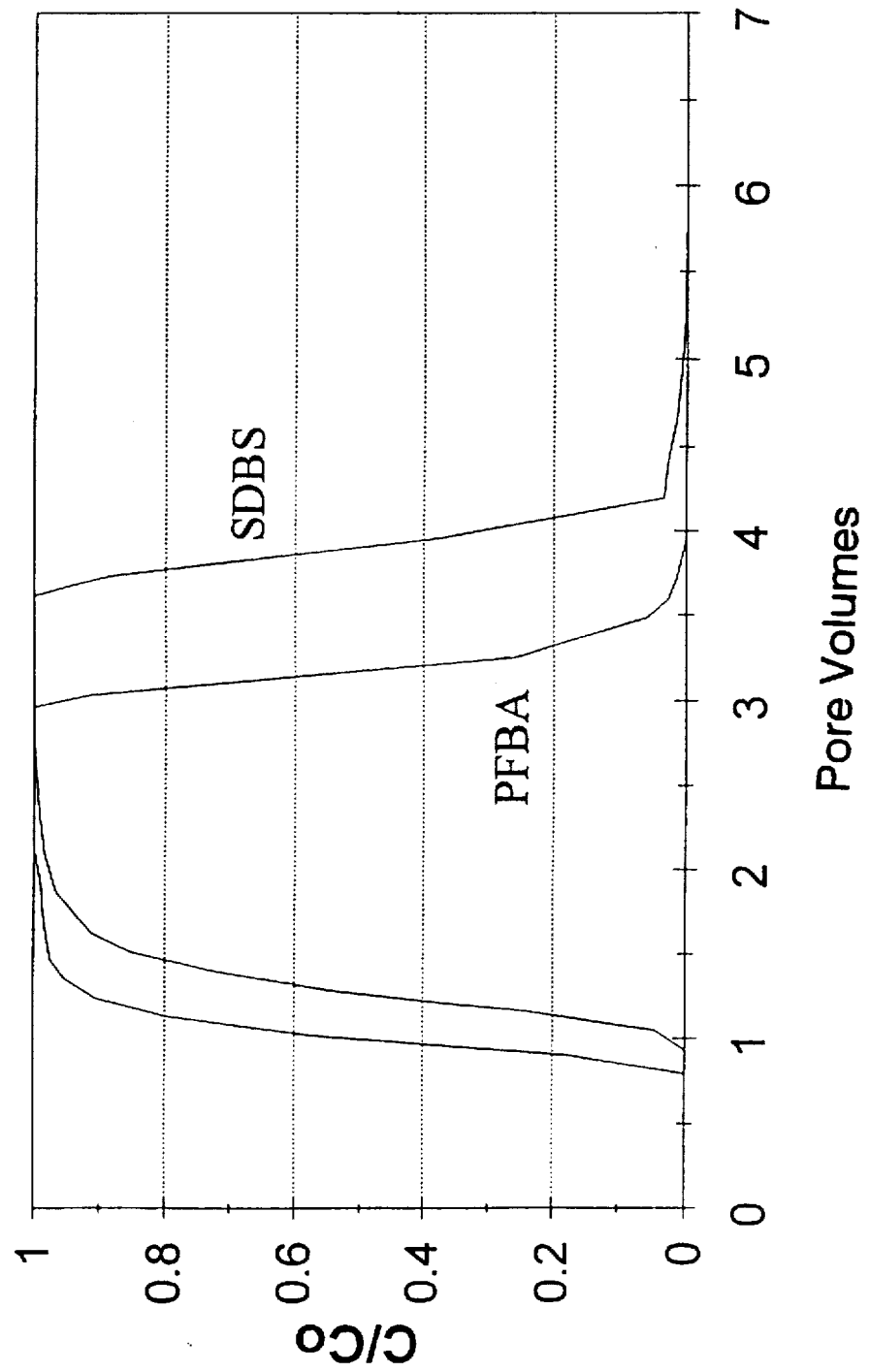
FIG. 3 is a graph of the changes in the relative concentration of non-reactive tracer (PFBA) and the interfacial tracer (SDBS) in effluent of sand-pack columns containing decane-water interfaces, where the cumulative effluent volume is represented as pore volumes.

In the decane-water experiments, we observed a bilinear trend in the $\gamma$ versus C plot for the adsorption of SDBS at the said fluid-fluid interface (FIG. 2), which is consistent with several earlier observations (8,17). The $\gamma$ versus C plot with an initial steep slope in the zero to less than 100 mg/L range, followed by a gentle slope from 100 mg/L to the CMC, results in a linear isotherm in the 100 mg/L to the CMC concentration range. The retardation of the interfacial tracer, SDBS, relative to that of a non-reactive tracer, PFBA, being displaced through packing of glassbeads containing decane-water interfaces is shown in FIG. 3. Furthermore, we observe (FIG. 4) that the SDBS interfacial adsorption isotherm, measured using the step input column techniques, can be approximated to be linear in the zero to CMC concentration range, which is a reasonable and useful approximation for tracer applications in hydrology and engineering. Such approximation enables one to define a Retardation Factor, $R_f$, as a linear function of $K_{ij}$ according to Eqn. 4, and thus simplifies the method application. Having measured $R_f$ from flow adsorption experiment, $K_{ij}$ is the only additional parameter required to estimate the $\alpha_{ij}$ of the porous medium using Eqn. 4.

A $K_{ij}$ value can also be approximated as the slope of the linear isotherm, as $\Gamma_{max}/\text{CMC}$, where $\Gamma_{max}$ is the maximum $\Gamma$ value corresponding to the CMC, and is equal to $1/N\alpha$. The parameters $\alpha$ and CMC can be measured for a given anionic surfactant and fluid-fluid interface, using the $\gamma$ versus lnC plots, or obtained from the literature. The oil saturation $S_n$ can be measured using partitioning tracers. Thus, after obtaining an $R_f$ value from the tracer experiment, Eqn. 4 can be used to determine the $\alpha_{ij}$, the only unknown.

Values of $\alpha$ reported for a number of anionic surfactants at air-water and heptane-water interfaces range from 45 to 72 $\text{Å}^2$. Oh and Shah estimated $\alpha$ of sodium dodecylsulfate at hexadecane/water and air/water interfaces as 68.9 and 5.18 $\text{Å}^2$ respectively. Sodium dodecylbenzosulfonate (SDBS), an anionic surfactant, exhibited saturation adsorption on graphon, a hydrophobic surface, at the CMC, with $\alpha$ value of 60 $\text{Å}^2$. We obtained $\alpha$ value of 61 $\text{Å}^2$ for SDBS at decane-water interface, from a plot of interfacial tension, $\gamma$, versus the lnC, using the Wilhelmy plate technique for measuring $\gamma$.

Using glass columns packed with different porous media (glass beads of approximately 500 to 100 microns size and clean sand) and SDBS as a interfacial tracer, we conducted adsorption experiments to measure decane-water $\alpha_{ij}$ values. A spectrophotometer was used for SDBS analysis. Decane was introduced in the porous media, using a syringe pump at a flow rate of 0.2 ml/min. A part of the decane was later removed by injecting water in an upflow mode into the initially decane saturated columns, at a flow rate of 0.5 ml/min. At the end of loading, pore spaces in the columns are filled partially with decane at a saturation $S_n$. Characteristics of experimental columns are presented in Table 1.

TABLE 1

Characteristics of Interfacial Tracer Experiment Columns

| Column | Length/dia cm | porous medium | pore volume P, ml | decane $S_n$ | mode of decane loading |
|---|---|---|---|---|---|
| IFT-O | 5 × 2.54 | clean sand | 9.70 | 0% | no decane |
| IFT-A | 15 × 2.54 | glass beads | 21.5 | 21.8% | decane first |
| IFT-B | 5 × 2.54 | clean sand | 8.1 | 12.3% | decane first |
| IFT-C | 5 × 2.54 | clean sand | 7.5 | 25% | water first |

Figure 4:
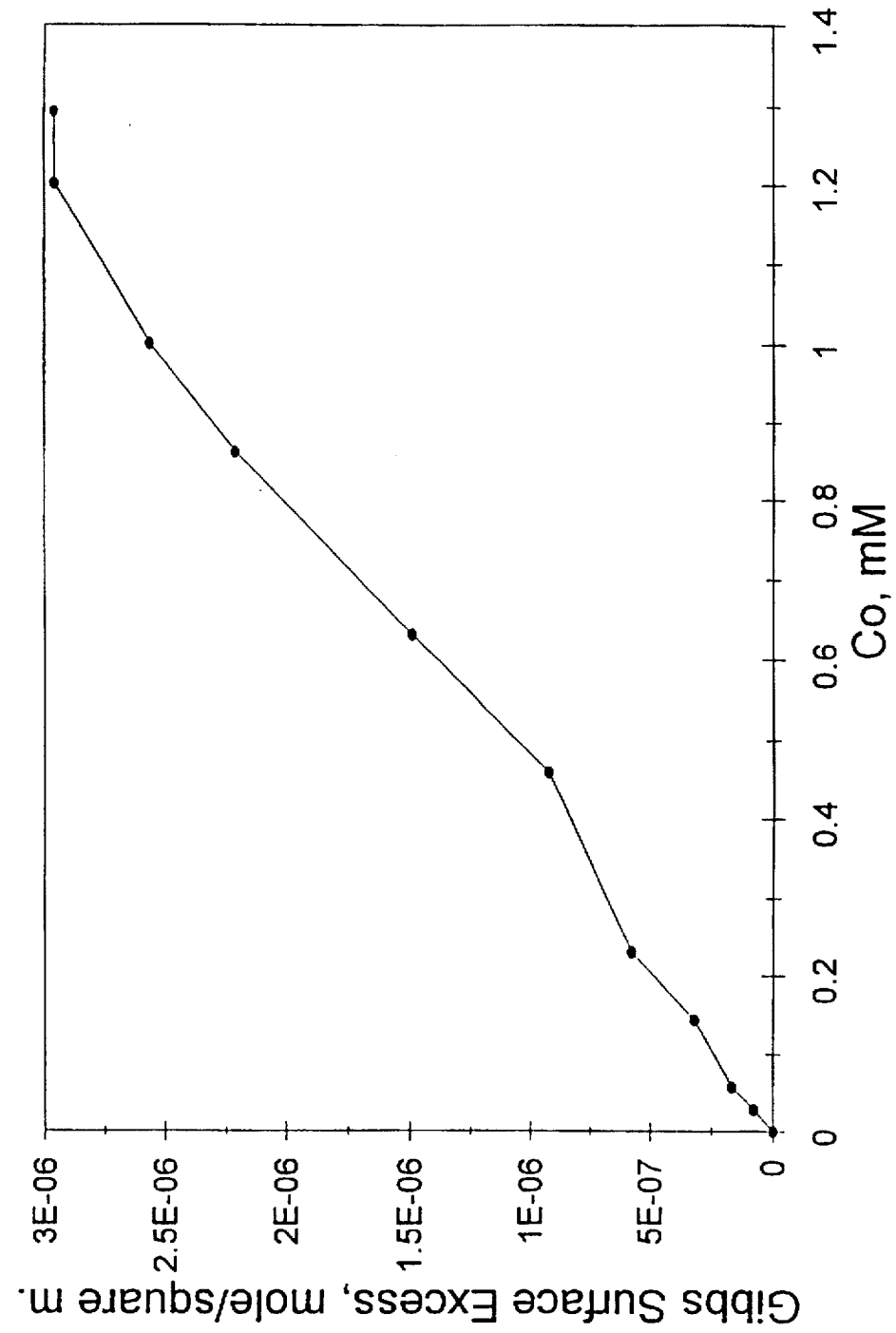
FIG. 4 is a graph of the isotherm for the adsorption of anionic surfactant SDBS at decane-water interfaces in columns of glassbead packings.

Results from column experiments are tabulated in Table 2. Isotherm for adsorption of SDBS at the decane-water interface for the columns, shown in FIG. 4, is linear. Each data point in those isotherms represents a $\Gamma$ value obtained from a column experiment at a $C_o$ value, using Eqn. 6. As can be seen from FIG. 2, slope of the $\gamma$-C plot is nearly constant in the 100 to 418 mg/L (CMC) tracer range, which explains the near linearity of the isotherms in this concentration range (FIG. 4). The $\Gamma$ values closely agree among three columns runs, and with earlier reported values for SDBS at a hydrophobic surface. The partition coefficient $K_{ij}$ values approximately as slopes of isotherms are in agreement between IFT-A and IFT-B columns. Column experiments could not be conduced with $C_o$ values well beyond the CMC, as the supra-CMC surfactant solutions can significantly dissolve and mobilize decane in the columns, thus changing the morphology and the $\alpha_{ij}$ value.

TABLE 2

Results of interfacial Tracer Experiments In Porous Media Columns

| Column | $a_v$, cm²/cm³ | $\Gamma_{max}$ moles/m² | K(m) |
|---|---|---|---|
| IFT-O | 0 | 0 | 0 |
| IFT-A | 480 | 2.73e-06 | 2.14e-06 |
| IFT-B | 511 | 2.72e-06 | 2.16e-06 |
| IFT-E | 162 | 2.73e-06 | 2.27e-06 |

Assuming smooth, cubical particles and typical grain size distributions, the specific surface area of porous media in our experiments can be estimated by geometric analysis to be in the range 300 to 500 cm²/cm³. However, irregular shape and surface roughness of particles can result in a higher specific surface area as measured by chemisorption techniques tan that obtained by geometric calculations. The specific surface area for the sand is measured by nitrogen atmosphere to be 1300 cm²/cm³ of sand. In the case of IFT-A and IFT-B columns, decane appears to have wet the dry solid surfaces as films. Thus, the $\alpha_{ij}$ values of 480 cm²/cm³ for decane coating relatively fine, dry glass beads and 511 cm²/cm³ gram for a relatively coarse sand are reasonable. Further the $\alpha_{ij}$ values, indicating the possible role of grain texture and surface roughness in spreading of NAPL on the surfaces. Overall, the results ($\alpha_{ij}$ values) are reasonable for the porous media used and are in agreement with the current understanding of immiscible fluid behavior in porous media.

In the case of solid-liquid interfaces, fine powdered adsorbents of known area, like graphon, are used to verify a technique proposed to measure specific surface area. In contrast, it is very difficult to create a large fluid-fluid interface of known area in an experimental system. Further, no other methods currently are available against which to verify the proposed method. However, considering that the specific surface area is a utilitarian rather than an absolute entity together with the strong indirect evidence provided, the proposed method merits application. In many porous media applications, one is interested in comparing interfacial areas among different systems, rather than measuring the absolute interfacial areas per se. For example, the proposed experimental technique can be used to define an 'oil-water interfacial area to oil volume ratio' (I), which is an index of how thinly spread the oil is in a porous medium. Between two porous media having the same oil saturation, the one containing many smaller oil blobs and films will have a higher I value, a result useful in the location of large pools of oils in aquifers and petroleum reservoirs. The I values for the columns IFT-B and IFT-C in our experiments are 4154 and 648 cm⁻¹ respectively.

EXAMPLE 2

Air-Water Experiments

Figure 5:
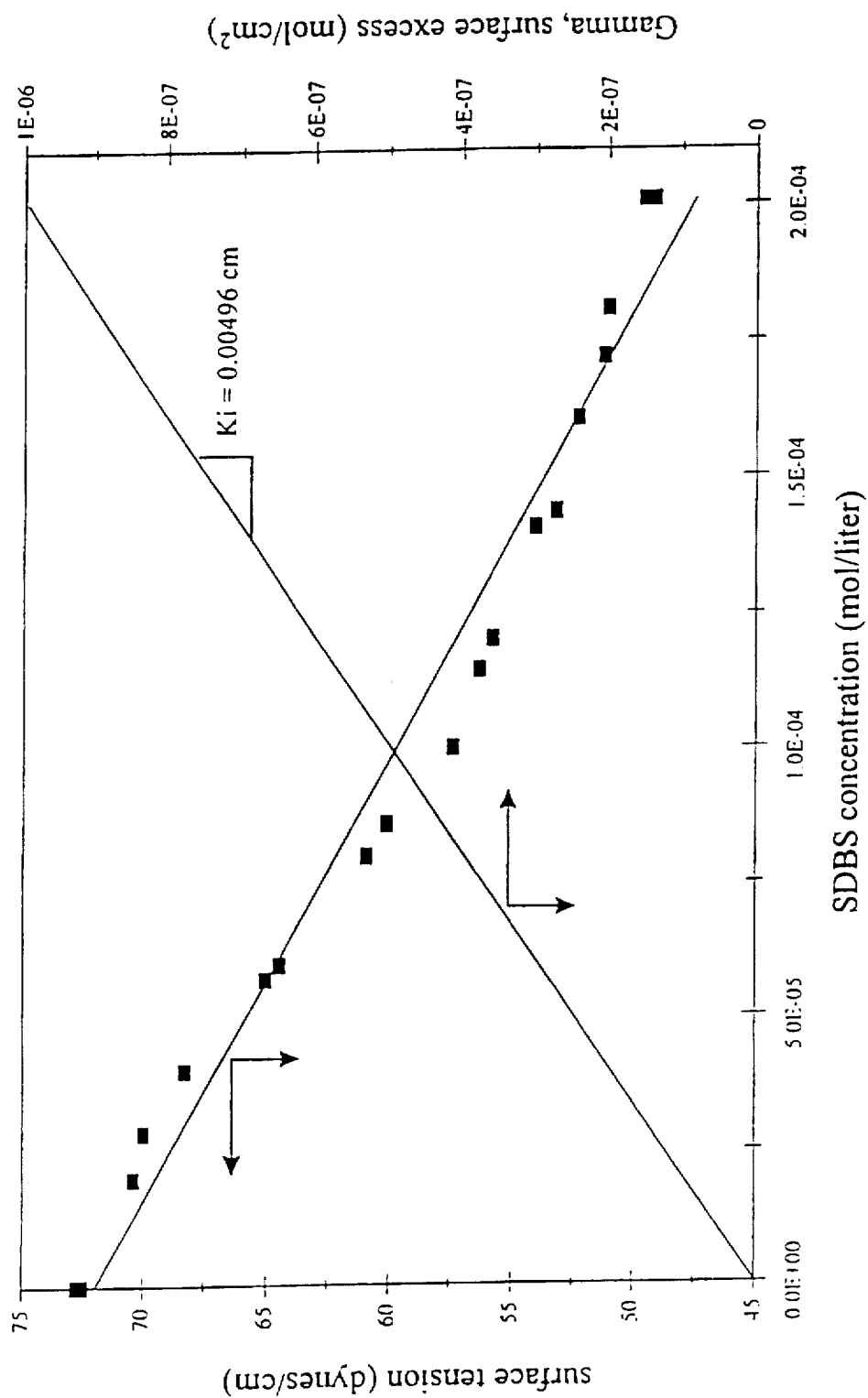
FIG. 5 is a graph of the change in Gibb's surface excess and interfacial tension due to sorption of the interfacial tracer (SDBS) at air-water interface.

In the air-water experiments, a linear trend in the γ versus C plot for air-aqueous solution interface (FIG. 5) was observed for the air-water interface, which is linear within the reported concentration range, and results in a linear isotherm. Thus, as shown in (FIG. 5) the isotherm can be approximated to be linear within the SDBS concentration range of zero to 2.0E-04M, which is a reasonable and useful approximation for tracer applications in vadose zone hydrology and engineering. The slope of this isotherm, denoted as $K_i$ in FIG. 5, is the equivalent of $K_{ij}$. A linear isotherm enables one to define a retardation factor $R_i$ as a linear function of $K_{ij}$ according to Eqn. 2, and thus simplifies the method application.

Having measured $R_i$ from flow adsorption experiment, $K_{ij}$ is the only additional parameter required to estimate the $\alpha_{ij}$ of the porous medium using Eqn. 4. In the present air-water experiments, the $K_{ij}$ value measured using the information of FIG. 4 is 0.00496 cm. After obtaining an $R_i$ value from the tracer experiment and water saturation $\theta_1$ measured using non-reactive tracers, Eqn. 4 can be used to determine the specific air-water interfacial area, $\alpha_{ij}$, the only unknown.

Figure 6:
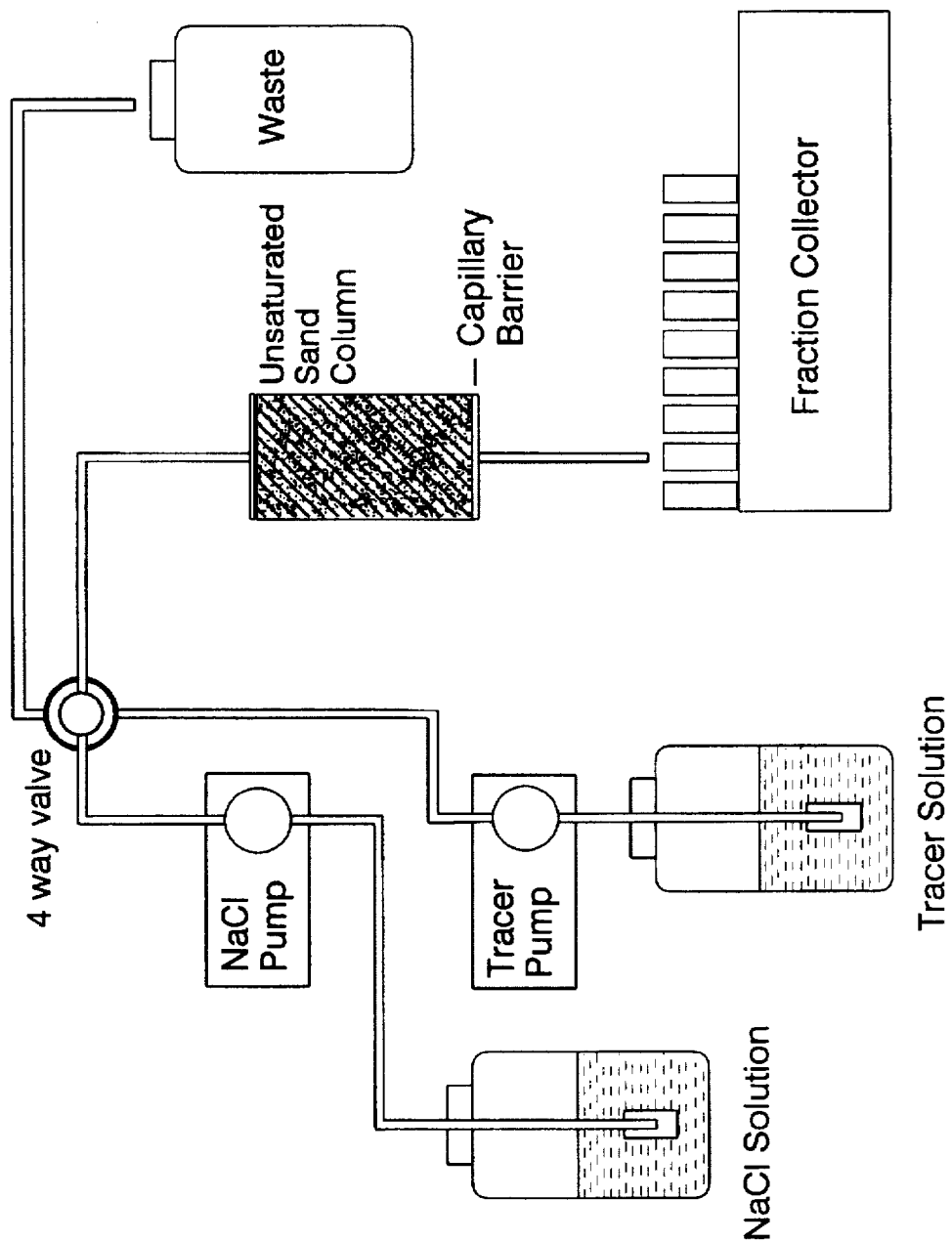
FIG. 6 is a graph of the schematic representation of the apparatus used to measure air-water interfacial areas in sand-pack columns.
Figure 7A:
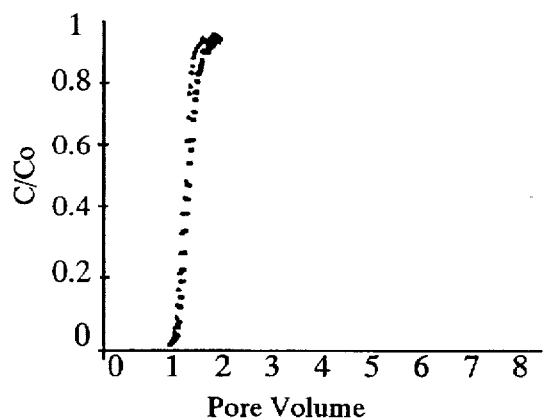
FIG. 7 is a graph of changes in the relative concentration of non-reactive tracer (bromide) and the interfacial tracer (SDBS) in effluent of sand-pack columns with air-water interfaces, where the cumulative effluent volume is represented as pore volumes.
Figure 7B:
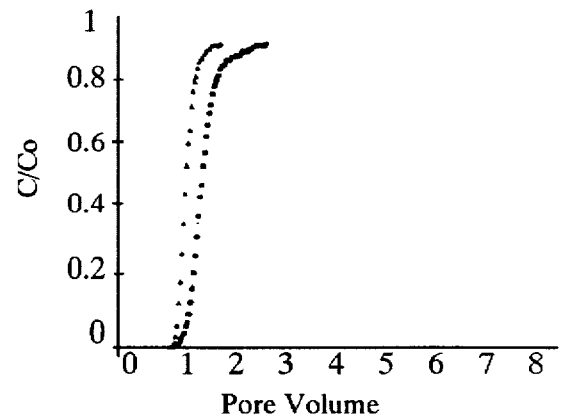
Figure 7C:
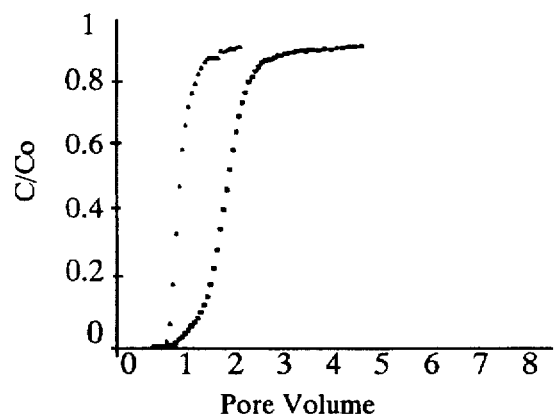
Figure 7D:
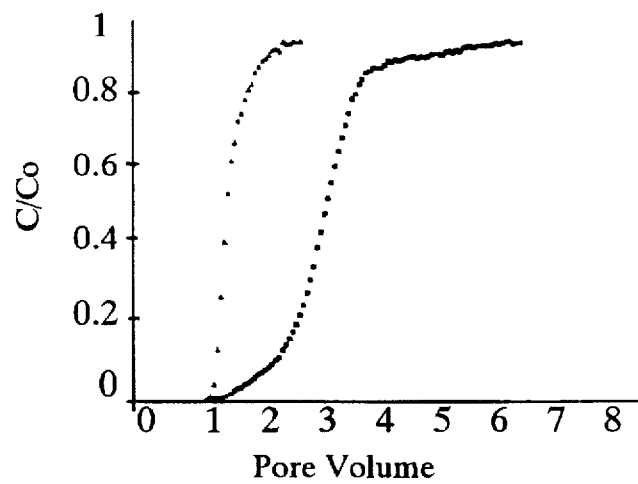
Figure 7E:
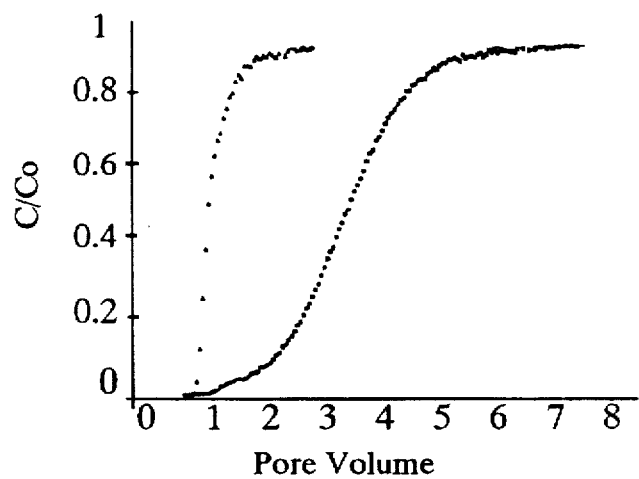

Using glass columns packed with clean sand, SDBS as a interfacial tracer and potassium bromide as non-reactive tracer, experiments were conducted to measure air-water $\alpha_{ij}$ values at different water contents. The experiments were conducted using SDBS in the presence of NaCl at two different concentrations, viz. 0.2 mM and 0.1 mM. The experimental apparatus used is shown in FIG. 6. A spectrophotometer was used for SDBS analysis. The retardation of the interfacial tracer, SDBS, with respect to the non-reactive tracer, Bromide, during displacement through sand-pack columns containing air-water interfaces, at various water contents, is shown in FIG. 7. The experimental conditions and results from these experiments are tabulated in Table 3. In this table, the experimental sets denoted I and II correspond to similar experiments, conducted using SDBS in the presence of two different NaCl concentrations, 0.2 mM and 0.1 mM, respectively.

Figure 8:
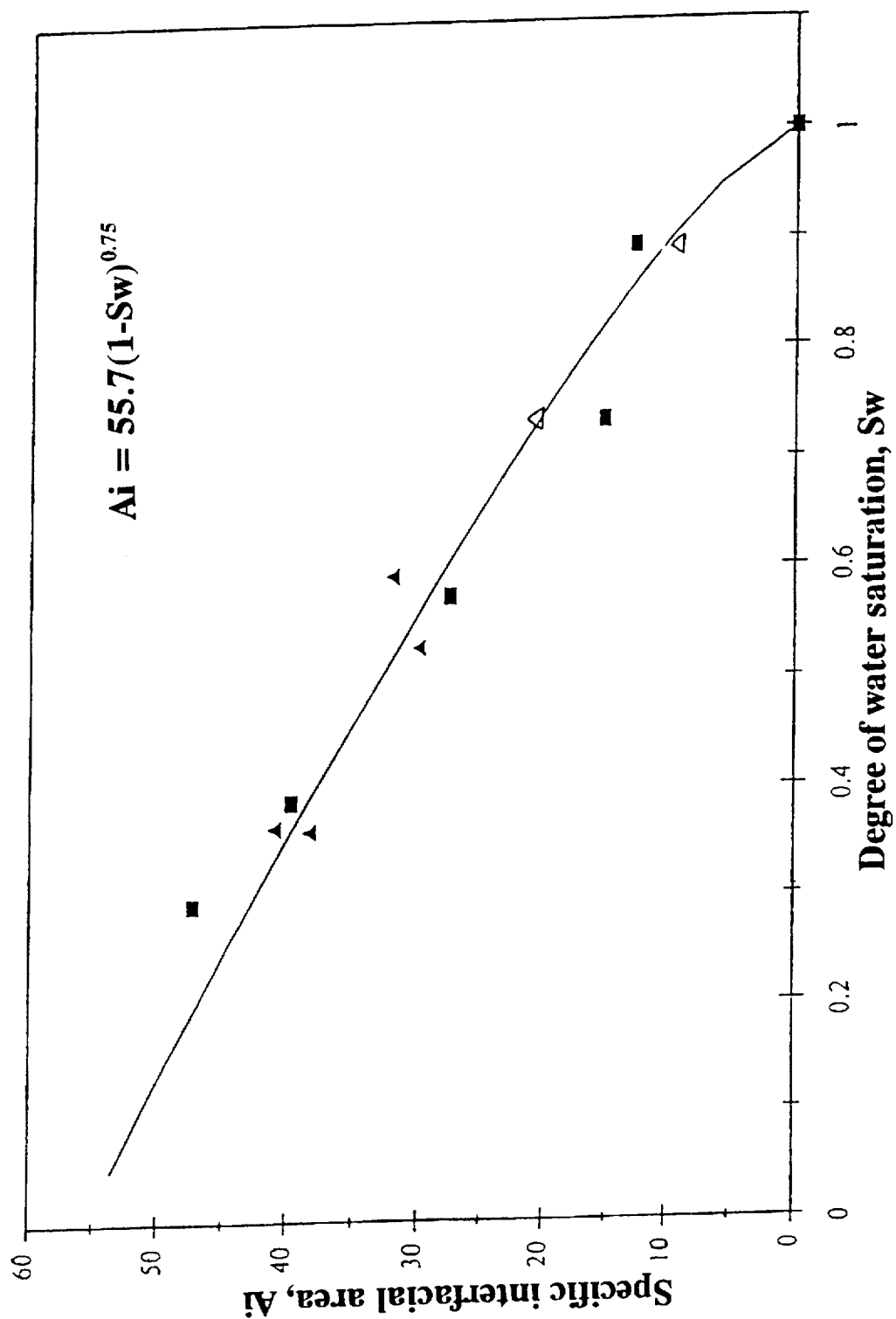
FIG. 8 is a graph of the air-water specific interfacial area in sand-pack columns increasing with decreasing water content.

The results clearly indicate that the specific air-water interfacial area $\alpha_{ij}$ increased as the water content in the sand column decreased (FIG. 8). This result is in agreement with the theory of immiscible fluid behavior in porous media. With decreasing water contents, as the air content in the sand increases and the average size of air pockets grows larger, the $\alpha_{ij}$ value also should increase. Overall, the results ($\alpha_{ij}$ values) are reasonable for the porous media used and are in agreement with the current understanding of immiscible fluid behavior in porous media.

The proposed technique finds immediate applications in groundwater remediation. Many groundwater contamination incidents begin with the release of immiscible, non-aqueous phase liquids (NAPLs) into the sub-surface, which are trapped in the sub-surface as blobs, wedges and films coating the aquifier solids, primarily under the influence of capillary forces. Owing to the complex shapes NAPLs assume, quantification of $\alpha_{ij}$ is essential for understanding the mass transfer and kinetics of dissolution of NAPLs in groundwater, and hence their mobilization and solubilization in chemically enhanced remediation.

We claim:

1. A method for measuring the surface area of immiscible fluid interfaces at a fluid-fluid interface in a flow system having a test volume containing at least two immiscible fluids therewithin either in the presence or absence of a solid phase, comprising the steps of:

providing in a first of said fluids an interfacial tracer compound soluble in said first fluid which will form a monolayer at the fluid-fluid interface when flown past second of said immiscible fluids, but which will not partition into the second of said fluids;

allowing for the said tracer compound to accumulate as a monolayer at the said fluid-fluid interface;

measuring the response of said tracer compound in the first of said fluids;

calculating the area of said interface by interpreting the measured tracer response.

2. The method of claim 1, wherein the first of said fluids, designated the carrier fluid, is moving past the second of said fluids.

3. The method of claim 1, wherein said first and second fluids are in contact with a solid phase comprising a porous medium.

4. The method of claim 3, wherein the calculation of the interfacial area $\alpha_{ij}$ (cm$^2$/cm$^3$) of an immiscible fluid interface in a porous medium of volume V (cm$^2$) is performed according to the equation:

$$a_{ij} = MN \frac{a}{Vm10^{19}} \quad (1)$$

where M (mg) is the mass of an interfacial tracer adsorbed at equilibrium from solution at critical micellar concentration (CMC), $\alpha$ (Å$^2$) is the area per molecule of tracer adsorbed at the interface at monolayer adsorption, N is Avogadro's number and m (gm/mole) is the tracer molecular weight.

5. The method of claim 2, wherein said tracer compound is added to the first of said fluids at a first, upstream position, and the quantity of said tracer compound remaining in said first fluid after formation of said monolayer is measured at a second, downstream position.

6. The method of claim 5, wherein a non-reactive tracer, which does not react in any way with second of said fluid is added to said first fluid at said upstream position, and the amount of said non-reactive tracer in said first fluid is measured at said downstream position.

7. The method of claim 6, wherein at least a portion of said first fluid is flown past said second fluid.

8. The method of claim 5, wherein said interfacial tracer is added to said first fluid as a pulse input.

9. The method of claim 6, wherein said interfacial tracer is added to said first fluid as a step input that provides complete coverage of the fluid-fluid interfacial area.

10. The method of claim 3, wherein the specific fluid-fluid interfacial area of the interface is calculated according to the equation:

$$a_{ij} = \frac{(R_t - 1)\theta_i}{K_{ij}} \quad (2)$$

wherein $R_t$ is a time delay retardation factor that represents retardation of the interfacial tracer (denoted by subscript IT) relative to the retardation of a non-reactive tracer (denoted by subscript NR) that does not react in any way with said second fluid, where said non-reactive tracer is given as:

$$R_t = \frac{\mu_{IT}}{\mu_{NR}} \quad (3)$$

$$\mu = \frac{\int_o^\infty C(t)t \, dt}{\int_o^\infty C(t)dt} - \frac{t_s}{2} \quad (4)$$

and C(t) is the eluent tracer concentration where Equation 4 is the integrated polynomial involving a tracer pulse centroid and $t_s$ is the time period during which the tracer pulse is introduced, $\Theta$ is the carrier fluid content expressed as a volumetric fraction, and $K_\mu$ is a linear adsorption coefficient, obtained as the slope of Gibbs' interfacial adsorption isotherm.

11. The method of claim 1, wherein said interfacial tracer includes, but is not limited to the following chemical classes: anionic surfactants, nonionic surfactants, fatty acids.

12. The method of claim 11, wherein said anionic surfactant is sodium dodecyl benzenesulfonate.

13. The method of claim 1, wherein said first fluid is water and said second fluid is one of the following: oil, organic liquid miscible with water, gas, air.

14. The method of claim 13, wherein said non-reactive tracer is pentafluorobenzoic acid or inorganic anion such as bromide, chloride and iodide.

15. The method of claim 1, wherein the concentration of said interfacial tracer compound in said first fluid is absorbed at equilibrium from solution at a critical micellar concentration.

* * * * *